(12) United States Patent  (10) Patent No.:  US 6,236,734 B1
Barry  (45) Date of Patent:  May 22, 2001

(54) DETECTION OF DEFECTS IN GLASS

(75) Inventor: John Cotter Barry, Durack (AU)

(73) Assignee: The University of Queensland, Queensland (AU)

( * ) Notice: Subject to any disclaimer, the term of this patent is extended or adjusted under 35 U.S.C. 154(b) by 0 days.

(21) Appl. No.: 09/194,399

(22) PCT Filed: May 28, 1997

(86) PCT No.: PCT/AU97/00336

§ 371 Date: Nov. 30, 1998

§ 102(e) Date: Nov. 30, 1998

(87) PCT Pub. No.: WO97/46869

PCT Pub. Date: Dec. 11, 1997

(30) Foreign Application Priority Data

May 31, 1996 (AU) ..................................................... P00235

(51) Int. Cl.⁷ ..................................................... G06K 9/00
(52) U.S. Cl. ........................................... 382/100; 392/141
(58) Field of Search ..................................... 382/100, 108, 382/141, 142; 356/429, 445, 237.1, 239.1, 239.3, 239.7, 239.8; 348/92, 143; 65/29.12, 158

(56) References Cited

U.S. PATENT DOCUMENTS 4,076,426 * 2/1978 Gross et al. ....................... 356/239.1
4,160,601  7/1979 Frosch .................................... 356/404
5,073,707 * 12/1991 Marcin .............................. 250/223 R
5,841,530 * 11/1998 Hewitt et al. ..................... 356/237.1

FOREIGN PATENT DOCUMENTS 0 282 687   9/1988 (EP) .............................. G01N/21/88
08304048   11/1996 (JP) ............................... G01B/11/30
WO 94/08229   4/1994 (WO) ............................ G01N/21/88

* cited by examiner

*Primary Examiner*—Andrew W. Johns
*Assistant Examiner*—Shervin Nakhjavan
(74) *Attorney, Agent, or Firm*—Akin, Gump, Strauss, Hauer & Feld, L.L.P.

(57) ABSTRACT

Defects in window glass, particularly nickel sulfide stones, are detected by photographing portions of the window glass onto photographic film in controlled lighting conditions, and then optically magnifying the photographic film images. The magnified images are visually examined to detect inclusions and/or other defects. Although the window glass is photographed on site, the magnified images can be examined later in more comfortable surroundings with the advantage of magnification. The photography is performed by a camera (12) mounted on a frame (13) which is releasably fixed to the building containing the window glass. A light source (11) is also mounted on the frame (13) to illuminate the window glass which is photographed at an oblique angle by the camera (12). Tie rods (31) extend into the mullion tracks of the building and can be retracted pneumatically to fix the frame (13) in position relative to the building.

11 Claims, 4 Drawing Sheets

DETECTION OF DEFECTS IN GLASS

DETECTION OF DEFECTS IN GLASS

This invention relates to a method and apparatus for detection of defects in glass. In particular, the invention is directed to a method and apparatus for locating nickel sulphide stones in tempered plate glass, although the invention is not limited to this particular use.

BACKGROUND ART

Nickel sulphide (NiS) stones are sometimes found as impurities in glass. It is known that such nickel sulphide stones cause spontaneous fracture in toughened window glass. The spontaneous fracture can cause serious problems in high-rise office buildings, where large areas of glass are used.

It is very difficult to detect the presence of NiS stones at the time of glass manufacture. The glass scanners on the glass production line cannot detect stones smaller than 1 mm in size. NiS is not a common impurity in glass and when it does occur, the stones range in size from 0.1 to 0.6 mm. It is believed that any nickel sulphide stone of diameter greater than 70 $\mu$m is capable of breaking toughened glass, but stones smaller than 70 $\mu$m do not normally break the glass.

Most batches of glass have very few nickel sulphide stones, but occasionally bad batches are produced. Problems resulting from the nickel sulphide impurities often do not become apparent until that glass is placed onto a building many months after manufacture. Consequently, it is very difficult for glass manufacturers to track down what actually caused the high incidence of NiS in that particular batch.

The applicant's earlier international patent application no. PCT/AU93/00498 described a method of detection of defects in glass under controlled lighting conditions. (The disclosure of that patent application is incorporated herein by reference). Although the method described in international patent application no. PCT/AU93/00498 was able to locate the majority of nickel sulphide stones in window glass, the method had a number of inherent disadvantages.

First, the method was conducted entirely on site, and hence was dependent on weather conditions. Secondly, the method was tedious and time consuming. Thirdly, the method did not located all problematic NiS stones, possibly due to lack of concentration by the person examining the windows as a result of tedium and uncomfortable environment.

It is an object of the present invention to provide an improved method and apparatus for detecting defects in window glass.

SUMMARY OF THE INVENTION

In one broad form, the present invention provides a method of detecting defects in window glass, comprising the steps of photographing portions of the window glass onto photographic film in controlled lighting conditions, optically magnifying the photographic film images, and optically examining the magnified images to detect inclusions and/or other defects.

In the method of this invention, only the "photographing" step need be conducted on site. Once the window glass has been photographed, the film images can be examined subsequently in more comfortable surroundings. The film images can therefore be examined more easily, and more accurately.

Further, since the photographic film images are magnified for examination, the observer has the advantage of magnification in detecting defects in glass (as compared with direct visual observation of the glass as described in our earlier patent application).

Preferably, the photographing step is performed using a camera mounted on a frame which is releasably fixed to the building containing the window glass being examined. The frame may be suitably fixed to the window mullions. The camera frame is located in the building maintenance unit (BMU), but is fixed relative to the window during photography.

Several cameras may be carried on a single frame, to maximise photographic coverage of the window glass.

During photography, the window glass is illuminated by a light source carried on the BMU which also carries the operator.

In order that the invention may be more fully understood and put into practice, a preferred embodiment thereof will now be described with reference to the accompanying drawings.

DESCRIPTION OF PREFERRED EMBODIMENT

Figure 1:
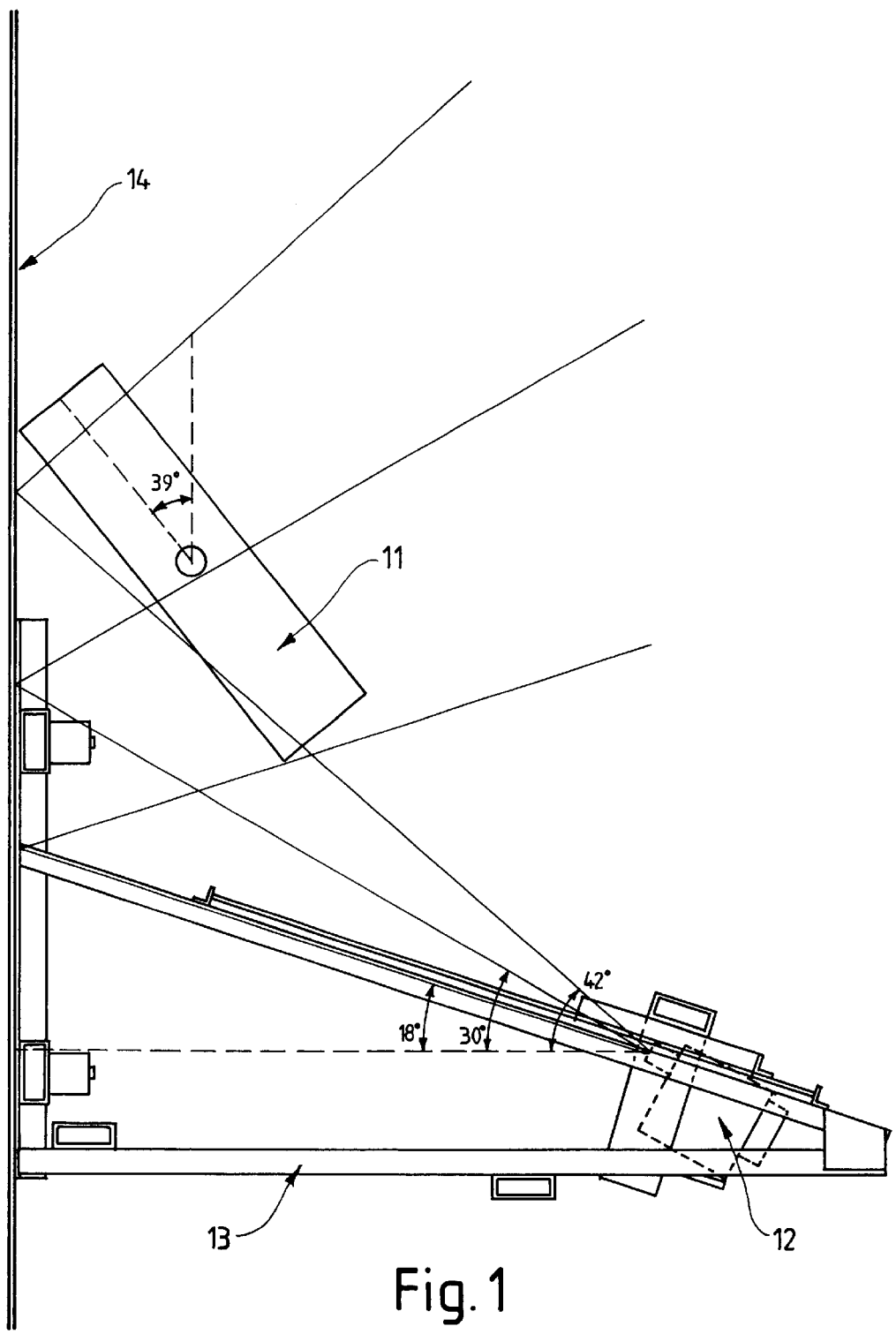
FIG. 1 is a schematic side elevation of apparatus for photographing window glass on site.

The apparatus used for photographing window glass is shown in FIG. 1. A light box 11 is attached to a building maintenance unit (BMU) and contains a suitable light source such as a set of fluorescent tubes, and is covered with a diffuser. The light distribution across the diffuser should be as uniform as possible. A camera 12 is supported in a frame 13 in the BMU, below the light box 11. The camera 12 and frame 13 are transported up and down the side of the building on the BMU. During the actual photography however, the camera frame 13 is locked to the side of the building by locating a suitable attachment (described below) within the window mullions. The operator stands within the BMU cradle.

Photography is performed at night, or in a darkened enclosure, to minimise effects of ambient light. With uniform illumination from the light box 11, the light reflected from the window 14 displays a uniform white background. Against this background, small stones or defects cast a dark shadow. In cases where the stone is at a position within the glass other than on the back surface, the stone appears as a double image. The first image is a direct image of the stone and the second image is the reflection of the stone in the back of the glass.

The photographs are taken with focus set at the surface of the glass while the window 14 is illuminated by the light box 11. All images are taken with the camera 12 set at the same working distance so that the overall object magnification is the same in all cases. The angle of tilt of the camera body, and the distance from the window to the front of the camera lens is determined by the choice of camera lens and the required size of the area photographed in each photographic exposure. The selection of specific values for camera tilt and working distance are discussed further below. The optimal camera working distance gives a demagnification of window to film of about 9 to 1 (on average).

After portions of the glass have been photographed onto negative films, an image scanning device (such as a microfiche reader) is then used to scan the films for defects. (Although the preferred embodiment uses a conventional microfiche reader adapted for use as the image scanner, any other suitable optical viewer may be used).

The microfiche reader has a 17 mm lens fitted and provides a magnification of 42×. The overall magnification of window to observed film in fiche reader is therefore 42/9, or about 4.5 times. That is, the image on the fiche reader is 4.5 times actual size on the glass. Therefore the observer has a 4.5 times advantage in seeing defects in the glass as compared with direct visual observation of the glass as taught in PCT/AU93/00498.

Particular aspects of the photographic method are discussed below, namely: (a) the type of film, (b) the type of camera, and (c) the type of camera lens, lens tilt, working distance, and area covered by each photograph.

a) The Type of Film

For the technique to be effective it is necessary to detect stones which are 70 μm (0.07 mm) in size and larger. In addition, the film resolution needs to be sufficient to take advantage of the optics of the camera lens. Film granularity and film contrast have an important effect on film resolution. To achieve the highest resolution, a fine-grained, high contrast film, such as AGFA ORTHO 25 is preferred. This film was compared with a number of other films types (such as KODAK TRI-X PAN and ILFORD PANF 50 Plus), and gave the best resolution of any films tried.

b) The Camera

The camera of camera is determined by a need to maintain the window surface in focus over the whole image and to capture the maximum amount of information on each photograph. Wide format cameras have an advantage over 35 mm cameras as they use a larger film area and therefore capture more information per photograph. Because the photographs are taken at an oblique angle rather than straight-on to the window, it is necessary to tilt the camera lens in order to maintain the whole image in focus. A FUJI GX680 II camera was used since it has lens tilt capability and uses 120 roll film with a film area of 76 by 55 mm (four and half times the area of 35 mm film).

c) The Lens, Lens Tilt, and Working Distance

For maximum efficiency, the largest possible area of glass should be captured on each photographic film while still having enough resolution to see a stone of 70 μm size. Empirically, it was found that for the GX680 II camera, a field on the glass of 600 mm width satisfies the resolution criterion while providing a reasonably large area of view.

A number of lenses were trialled. Lenses of short focal length are most desirable since with a short focal distance it is possible to bring the camera close to the glass and thus reduce the size of the frame required to hold the camera. However, lenses of very short focal length were found to have curved focus fields such that the images of the glass were unfocussed at the edges of the image field. The lens of shortest focal length that was found to have a suitably flat focal field was a 125 mm lens. For a 125 mm lens with a camera tilt angle of 30° and a horizontal field of 600 mm, the lens to window distance is 1018 mm.

The lens tilt can be found empirically by focussing to the centre of the screen and adjusting the lens tilt until both bottom and top of the image are in focus at the same time. The amount of lens tilt required may also be calculated by using a ray tracing method. The lens tilt required is equal to the tilt of the camera divided by the magnification. (For this case the camera was tilted at 30° from horizontal, the magnification in the image is 9 to 1, and so the tilt should be 30/9=3.3°. The lens tilt set empirically was found to be 3.2°. Within measurement error, the calculated tilt is equivalent to the empirical tilt setting).

The Camera Frame

Figure 5:
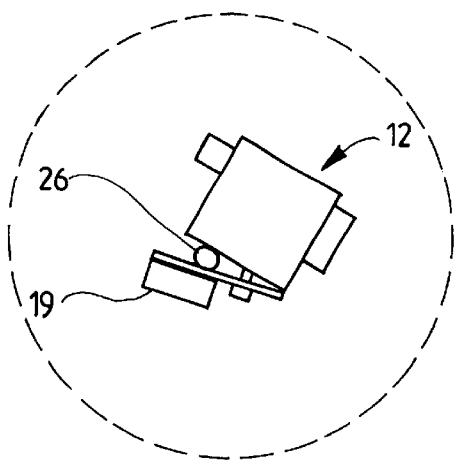
FIG. 5 is a fragmentary view of the camera fixed to the camera frame of FIG. 3.

In order to photograph windows from the BMU, a stable platform is required. Merely resting the camera on the BMU cradle is not normally satisfactory because the BMU cradle tends to move about. Although the light 11 is attached to the BMU cradle above the camera 12 small movement of the light will not affect the image, but any movement of the camera during an exposure will blur the image. The camera 12 is therefore mounted on a camera frame 13 which is adapted to be releasably affixed to the building. The design of the camera frame 13 is shown schematically in FIG. 2, and in more detail in FIGS. 3, 4, 5.

The frame 13 fixes the camera 12 at a set position and angle from the window 11 to be photographed. In this embodiment, the frame 13 is attached to mullion tracks on the building. (On a building without mullion tracks, any suitable alternative method for attaching the frame to the building may be used).

Figure 2:
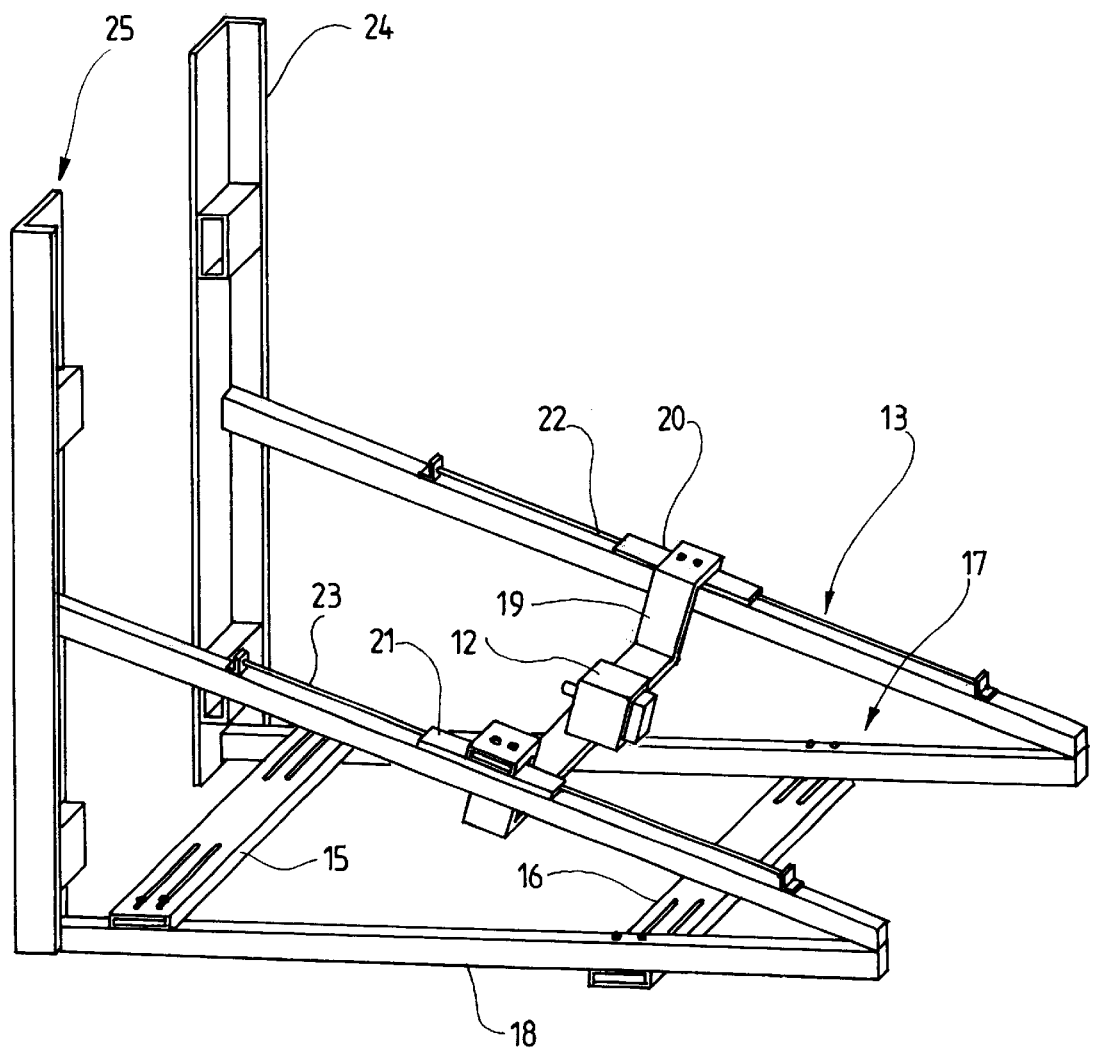
FIG. 2 is a perspective view of the camera frame used in the apparatus of FIG. 1.

The frame 13 has several advantageous features, including i) The frame is affixed to the window by a set of four pneumatic rams. The rams pull up against clamps located within the mullion guides on the building.

ii) The frame has an adjustable width (adjustable distance between the uprights which clamp to the mullions, FIG. 2) to suit various window widths.

iii) The camera is mounted on a cross-beam which may slide back and forth. The camera in the back position is at the correct distance for photography. The camera is able to be moved forward so that the film may be changed by an operator standing within the BMU.

A schematic of the frame is shown in FIG. 2. Thus, the frame is suitably built from a light material such as aluminium. Front and rear cross-beams 15,16 are welded at one end to the base member 17 of a triangular frame, and are slot and bolted at the other end to the base member 18 of a parallel triangular frame, to allow for adjustment of the frame spacing to individual window widths. The camera support 12 is mounted on a cross-beam 19 which is slot and bolted on both ends to respective slides 20, 21 which ride on slide rails 22, 23 of the triangular frames. The arrangement of the camera support cross-beam 19 is such that the camera 12 sits as low as possible within the frame 13.

Figure 3:
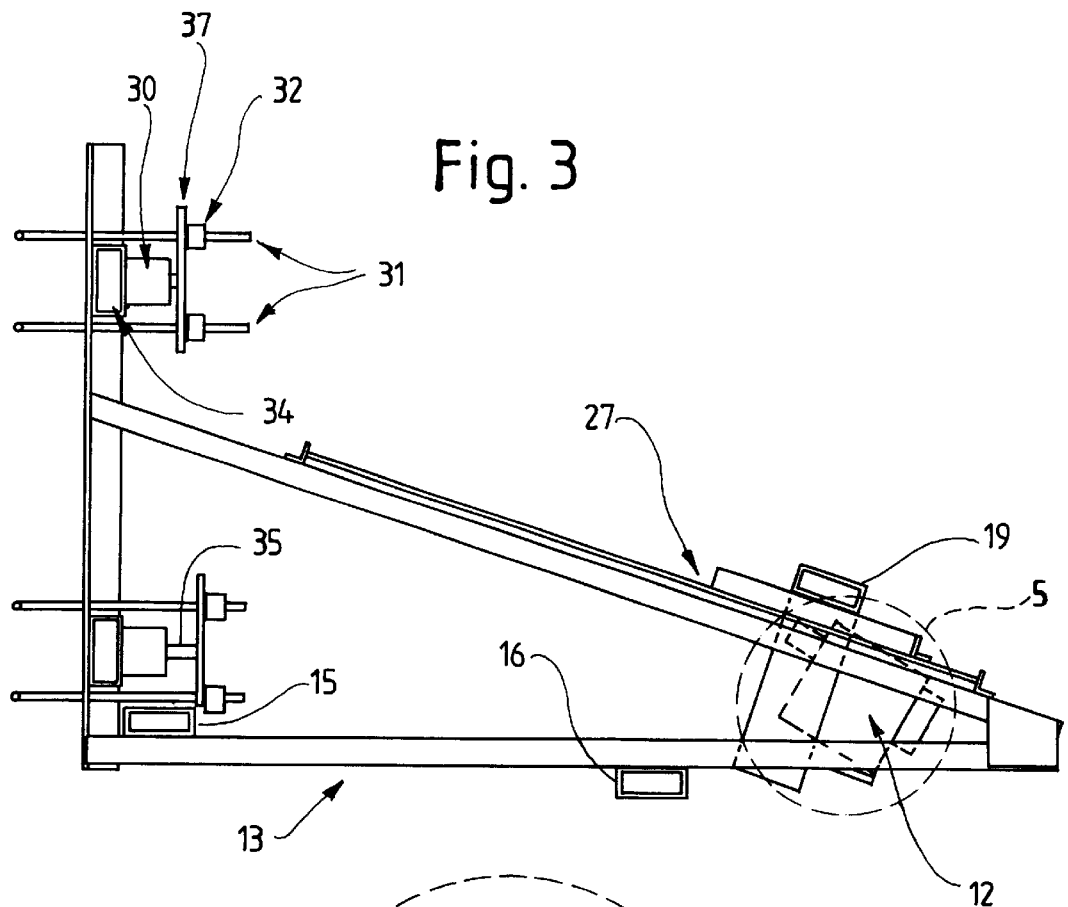
FIG. 3 is a side elevation of the camera frame of FIG. 2, with means for fixing the frame to the window mullions.

The frame 13 is shown in greater detail in FIG. 3. The camera 12 (drawn schematically) is shown in position on the frame, and also it is shown in more detail separately. The camera is at a tilt of 30° from the horizontal. Of the 30°, the design of the frame itself sets the camera slide at 18° from the horizontal. The remainder of the 30° is set by placing a spacer 26 on the camera support 19 which pivots the camera on that support. The camera 12 is normally secured to the support using its tripod attachment. The camera support and camera assembly can slide back and forth on a roller rail system 27. The two rollers on each rail are bolted together using a 300 mm long piece of 100×12 mm plate.

Four pneumatic rams 30 are used to attach the frame 13 to the mullions. Each ram 30 is fixed to a set of two tie-rods 31. The arrangement of the rams and tie-rods is shown schematically in FIG. 4. Each tie rod 31 has a T-shaped end. The other end of the tie-rod is threaded and has an aluminium alignment knob 32 screwed onto it. The alignment knobs 32 are locked in position with locking nuts.

Figure 4:
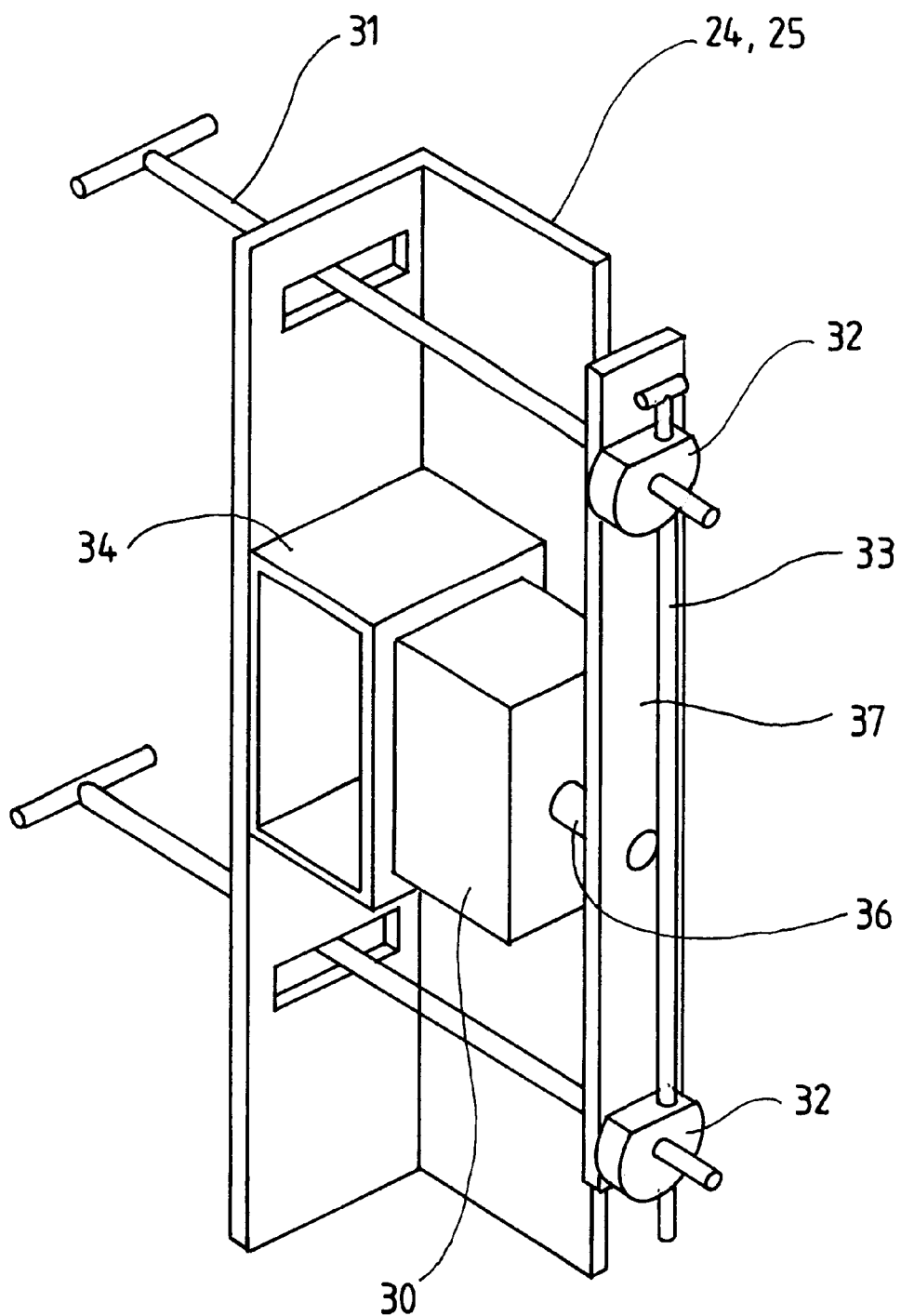
FIG. 4 is a schematic perspective view of the means for fixing the camera frame to the window mullions.

There is usually a 20 mm gap in the mullions between each window. To fix the frame 13 to the windows, the tie rods 31 are inserted into the mullion guides between the two windows with the T-shaped ends set vertically. The T ends are then rotated 90° so that the T ends are captive in the gap between the windows. Each of the alignment knobs has a hole drilled at one side so that an alignment pin 33 may be passed through both the top and bottom alignment knobs 32 of a particular ram assembly (FIG. 4). The alignment pin 33 locks the tie-rods 31 against any rotation so that the T ends remain in a horizontal position within the mullion guides.

The tie rods 31 pass through slots in the upright members 24, 25 of the transfer frames. The uprights 24, 25 are slotted for two reasons. First, the slots are wide enough to allow the T ends on the tie rods to be pulled back through the uprights so that they will not catch on anything when the BMU is being launched over the side of the building. Secondly, although the uprights are set at a spacing which corresponds to the window width, the mullion tracks are not exactly straight and the slots allow some lateral movement of the tie-rods to compensate for the small differences in spacing of the mullion tracks as the frame is moved down the building.

In the illustrated design, the rams push to lock on. The body of each ram is bolted to a ram support 34. The thrust shaft 36 of each ram 30 is attached to a plate 37 through which the tie rods 31 are inserted.

To attach the frame to the window, the tie rods are located in the mullion guides as described in the previous paragraph and turned. Compressed air is applied to the rams so that the ram thrusters 36 push out to cause the tie-rods 31 to be pulled outwards, which in turn, causes the T ends to pull up against the mullion guides at the back of the windows. This action pulls the frame against the front of the windows. The uprights 24, 25 suitably have 3 mm thick neoprene rubber sheet covering the surface facing the window so that the uprights will not damage the window surface. In addition the neoprene rubber provides a high friction surface which ensures that the frame does not slip when it is attached to the window.

The rams 30 are bi-directional so that they may be released merely by reversing the direction of the compressed air. There are "quick-connect" air-hose fittings on the air lines between the cross-bar and uprights. The air-lines are so arranged so that the camera frame can be disassembled if necessary. The air from the compressor passes through a four-way valve which is fixed to the front cross bar. By turning the handle on the four-way valve through 90° it is possible to reverse the air flow to the rams and so switch them from "off" to "on" and vice versa.

The light box 11 is fixed to the BMU cradle in a position relative to the camera as shown in FIG. 1. The light box is placed so as to provide illumination of the glass viewed by the camera (without obstructing the camera view of the window). To obtain the most even illumination the light box is tilted to 30° from the vertical. The camera is arranged to be as low as possible in the frame so that the light can also be kept as low as possible.

The Operation of the Camera and Frame

For window widths of up to 1800 mm three cameras 12 are required to order to be able to photograph the entire window width in a single session.

Once the BMU is at the desired position for photographing, the tie-rods are located the in mullion tracks, rotated and locked. The frame is now attached to the mullion tracks so that it cannot come away, although the tie-rods may slide down the tracks as the BMU cradle is lowered. For photography, the frame is lifted clear of the BMU cradle and fixed to the building by activating the pneumatic rams. After each photograph the pneumatic rams are released and the BMU is moved down into position for the next photograph.

Examining the Film

After the windows have been progressively photographed, the films are viewed in a microfiche reader, typically in a viewing room, and scanned for defects. The film carriage of a conventional fiche reader is modified so that it will take 120 roll film, and has a guide track added. The guide track moves the film 6 mm horizontally at each step and 4.5 mm vertically at each row. These correspond to distances of 250 mm horizontally and 190 mm vertically on the fiche screen. The fiche screen has dimensions of 350 by 270 mm and such steps present each section of film in turn for examination and ensure that there is ample overlap between adjacent fields. Viewing on the fiche screen gives a 4.5 times advantage as compared with viewing the glass directly. Each 250 mm by 190 mm area on the fiche screen corresponds to an area of 54 mm by 40 mm on the actual window.

In scanning the film the defects appear as white dot-pairs on the negatives. (The defects appear as black dots when viewed directly by the camera, but this is a negative film so the contrast is reversed). The dot-pairs may appear as strong white dots or as weak white dots depending on the size of the stones in the window. Having scanned one section of film, the examiner moves the film carriage to the next point on the guide track, and so on until all the film has been scanned.

The dot-pair distance is given by the formula:

$$D \text{ (dot-pair distance)} = 2T \tan\{\arcsin[\cos(\alpha)]/n\} \quad (1)$$

where T is either the glass thickness or the distance of the stone from the back of the glass, $\alpha$ is the light-to-film angle, and n is the refractive index of the glass. The light-to-film angle varies from point to point on the film although it has an average value of 30° (the camera tilt angle). A chart may be compiled for dot-pair distances (D) for marks on the surface of the glass for all film positions on the fiche guide track. The dot-pair distance chart is compiled from a photograph of a window which has had a set of marks placed on it with marker pen.

When a dot-pair is found, the spacing between the dots is measured and is compared with the spacing expects for a mark on the surface of the glass. If the spacing is the same as that expected for a mark on the surface of the glass, these dots are ignored. However, if the spacing is less than expected for a surface mark, the position of the dot-pair is recorded on a log sheet. An x,y calibration chart is then used to relate the x,y position of the defect on the film to an x,y position on the window. The depth-in-glass of the defect is calculated by taking the ration of the spacing of the dot-pair to the spacing expected for a mark on the surface of the glass. If the depth-in-glass ratio is between 20% and 80%, the stone is in the tension zone of the toughened glass and could cause glass fracture. If the ratio is not between 20% and 80% the stone is in the compression zone and is of no particular interest.

Final On-Site Examination of Stones

By examination of the film it is possible to tell when a stone is present but it is not always possible to discern the nature of that stone. For stones found in the tension zone it is advisable to go back to the windows to view those stones through a 10× magnifier to see whether they are nickel sulphide or not. Since the x,y position of each stone is calculated from their position on the film, it is easy to find these stones in the windows. When a window is found with a yellow stone which looks like nickel sulphide, that window should be removed. If the stones are not yellow in colour they may be considered to be passive.

The abovedescribed technique was trialled on 72 windows, and appeared to find all stones of 70 µm diameter and greater. The results of the photographic method were checked visually using two times magnification on four of the 72 windows. The photographic method was found to have located all stones that could be found in the most careful visual examination.

The foregoing describes only one embodiment of the invention, and modifications which are obvious to those skilled in the art may be made thereto without departing from the scope of the invention. For example, the above-described method can be used, with suitable modification, in quality control on glass float lines. Samples from the float line can be photographed, and later examined to give the manufacturer an indication of when nickel sulfide is forming. Such information may give the manufacturer the opportunity to relate conditions in the melt tank to the appearance of nickel sulfide in the glass.

Further, the progressive photography of window glass on a building may be automated or semi-automated, using computer control. For example, a microprocessor control circuit may be used to repeatedly release the tie rods, raise or lower the camera frame a predetermined distance, reapply the tie rods and fix the frame relative to the window, take photographs, and repeat the process until an entire column of windows has been photographed.

In yet another embodiment, the optical examination of the photographic film images may be performed, either on site or elsewhere, by automated or semi-automated inspection apparatus. Such apparatus can use software to perform pattern recognition to locate pairs of images on the film corresponding to NiS stones and their reflections.

On a building without mullion tracks, the frame may be suitably attached to the building by use of vacuum pads which are affixed to the windows on either side of the window to be photographed. The vacuum pads can be activated using a vacuum pump carried on the BMU.

It should also be noted that the step of photographing portions of the glass onto photographic film can be replaced by capturing images of the glass portions in digital data form (e.g. using a digital camera) providing that the required degree of resolution is achieved.

What is claimed is:

1. A method of detecting defects in window glass, comprising the steps of photographing portions of the window glass onto photographic film in controlled lighting conditions;

optically magnifying the photographic film images; and optically examining the magnified images to detect any one of inclusions and other defects.

2. A method as claimed in claim 1, wherein the photographing step is performed on site using at least one camera mounted on a frame releasably fixed to a building in which the window glass is fitted.

3. A method as claimed in claim 2, wherein the camera is a wide format camera having a focal length of about 125 mm.

4. A method as claimed in claim 1, wherein the portions of the window glass are photographed sequentially by a camera at a substantially constant distance from the portions being photographed.

5. A method as claimed in claim 1, wherein the portions of the window glass are photographed at an oblique angle.

6. A method as claimed in claim 1, wherein the film is a fine grained, high contrast film and the film images are magnified so that the magnified images are about 4.5 times actual size.

7. A method as claimed in claim 1, wherein the photographing, magnifying and/or examining steps are automated or semi-automated.

8. A method of detecting defects in glass, comprising the steps of recording images of portions of the glass;

magnifying the recorded images; and visually inspecting the magnified images at a location remote from the glass to detect any one of inclusions and other defects.

9. Apparatus for detecting defects in window glass on a building, comprising a movable frame, at least one camera mounted on the frame, a light source for illuminating the window glass to be photographed mounted on one of the frame and camera, and means for releasably fixing the frame to the building such that the camera is stationary relative to the window glass being photographed and a focal access of the camera is oriented obliquely to a plane of the window glass.

10. Apparatus as claimed in claim 9, wherein the fixing means comprises a plurality of clamping devices adapted to clamp the frame to mullion tracks on the building.

11. Apparatus as claimed in claim 9, wherein the frame is of adjustable width, and wherein the camera is adjustably mounted on said frame.

* * * * *